| United States Patent [19] | [11] Patent Number: 4,923,400 |
| Suzuki et al. | [45] Date of Patent: May 8, 1990 |

[54] DENTAL ADHESIVE COMPOSITION

[75] Inventors: Kunitomo Suzuki, Odawara; Takao Kiyohara, Fujisawa; Shinya Kitoh, Ito, all of Japan

[73] Assignee: Lion Corporation, Tokyo, Japan

[21] Appl. No.: 170,371

[22] Filed: Mar. 18, 1988

[30] Foreign Application Priority Data

Mar. 18, 1987 [JP] Japan .................. 62-64997

[51] Int. Cl.$^5$ .............................. A61C 5/04
[52] U.S. Cl. .................. 433/226; 106/35; 260/998.11; 526/312; 562/443
[58] Field of Search ............ 106/35; 433/226; 562/443; 260/998.11; 526/312

[56] References Cited

U.S. PATENT DOCUMENTS

| 4,323,348 | 4/1982 | Schmitz-Josten | 106/35 |
| 4,373,036 | 2/1983 | Chang et al. | 106/35 |
| 4,515,930 | 5/1985 | Omura et al. | 106/35 |
| 4,542,167 | 9/1985 | Aoki | 106/35 |
| 4,569,955 | 2/1986 | Dhabhar | 106/35 |

FOREIGN PATENT DOCUMENTS

| 52-113089 | 9/1977 | Japan. |
| 53-110637 | 9/1978 | Japan. |
| 2045960 | 3/1980 | United Kingdom. |

OTHER PUBLICATIONS

Kubota, "Adhesiveness of Resin Cements to Ceramics", Dental Materials; Devices, 3, No. 6, pp. 739-746, 1984.

Primary Examiner—Paul Lieberman
Assistant Examiner—Willie J. Thompson
Attorney, Agent, or Firm—Birch, Stewart, Kolasch & Birch

[57] ABSTRACT

A dental adhesive composition containing a compound having the formula (I):

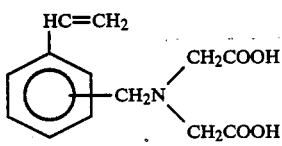

15 Claims, No Drawings

DENTAL ADHESIVE COMPOSITION

BACKGROUND OF THE INVENTION

1. Field of the Invention

The present invention relates to a dental adhesive (or cement), composition usable for adhering and firmly fixing dental restorative materials comprising ceramics such as calcium metaphosphate crystallized glass, and further, for example, alloys, porcelain materials, and/or composite resins, to the teeth.

2. Description of the Related Art

Various dental adhesives have been utilized for the therapy of teeth suffering from caries, such as zinc phosphate cement, carboxylate cement, glass ionomer cement, etc. Further, in recent years, as a newer type of dental adhesive, composite resin cements containing a vinyl monomer having phosphoric acid group or carboxylic acid anhydride group in the molecule, such as 4-methacryloxyethyltrimellitic acid anhydride and methacryloxyethlyphenyl hydrogen phosphate, are now commercially available. This composite resin cement can be used for the adhesion of a crown, or inlay to the teeth, and further, can be itself utilized as a dental restoring material by reinforcing the adhesion to the teeth by using another dental adhesive composition in combination therewith.

On the other hand, aesthetic considerations in dentistry have become important recently, and various new material ceramics have been developed in response to this need. Particularly, because castable ceramics such as calcium metaphosphate crystallized glass have characteristics similar to natural teeth in mechanical strength and the aesthetic sense, they are suitable for use as a dental restorative material. However, when utilizing such a material, a dental adhesive composition must be used for adhering and firmly fixing the dental restorative material comprising castable ceramics.

However, the dental adhesive composition of the prior art, although having a good adhesive force between teeth and a dental restorative material comprising, for example, an alloy, a porcelain material, or a composite resin, is not able to firmly adhere the dental restoring material comprising castable ceramics to the teeth, and a dental adhesive composition for such castable ceramics has not been proposed in the prior art.

Accordingly, a dental adhesive composition effective for adhering and fixing a dental restorative material comprising castable ceramics such as calcium metaphosphate crystallized glass to the teeth is desired.

SUMMARY OF THE INVENTION

Accordingly, the object of the present invention is to obviate the above-mentioned problems and to provide a dental adhesive composition having an excellent adhesive force between a dental restorative material comprising, for example, an alloy, a porcelain material, or a composite resin and teeth, and capable of adhering and stably and firmly fixing a dental restoring material comprising castable ceramics such as calcium metaphosphate crystallized glass to teeth.

Other objects and advantages of the present invention will be apparent from the following description.

In accordance with the present invention, there is provided a dental adhesive composition comprising a compound having the formula (I):

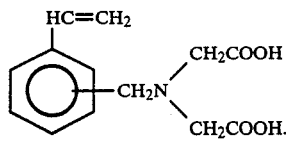

DESCRIPTION OF THE PREFERRED EMBODIMENTS

The present inventors have found that a product obtained by polymerization and curing of a compound represented by the above-mentioned formula (I) can be firmly adhered and fixed to a dental restorative material comprising castable ceramics such as calcium metaphosphate crystallized glass, even in saliva, that a polymer of such a compound of the formula (I) or a copolymer thereof with another polymerizable monomer is excellent as the adhesive for the dental restorative material comprising castable ceramics such as calcium metaphosphate crystallized glass, and further, that it is suitable as an adhesive for the dental restorative material comprising, for example, an alloy, a porcelain material, or a composite resin, and therefore, that a dental adhesive composition containing the compound of the formula (I) is free from the formation of gaps between the teeth and the dental restorative material or drop-off of the dental restorative material due to poor adhesion and can remarkably improve marginal leakage, thereby effectively inhibiting secondary caries, to accomplish the present invention.

The dental adhesive composition according to the present invention contains the compound of the formula (I) as mentioned above, and is adhered to the teeth by curing in use, and is used for the purpose of adhesion to the teeth, such as for adhesive or adhesion enhancement for adhering the dental restoring material prepared with ceramics, and further, for example, dental alloys and porcelains, to the teeth.

According to the present invention, the (N,N-dicarboxymethyl)aminomethyl group in the compound (I) may be at any position of ortho-, meta- and para-positions of the benzene ring of styrene, but particularly preferably is positioned at the meta-position or the para-position. The compound having the formula (I) is contained as a monomer in the present dental adhesive composition.

The dental adhesive composition according to the present invention may contain any other components, depending on, for example, the kind of the adhesive composition and the purpose of use. For example, when the present composition is used as the adhesive for adhesion between the teeth and the dental restorative material, only the compound having the formula (I) can be used as the adhesive monomer and, when used, the composition is polymerized and cured in the presence of a curing agent. However, generally speaking, the compound having the formula (I) is mixed with another polymerizable monomer, and the monomers are polymerized and cured in the presence of a curing agent when used.

In the above-mentioned case, examples of another polymerization monomer are one or more monomers selected from the group consisting of (a) styrene, (b) acrylic acid and derivatives thereof, and (c) methacrylic acid and derivatives thereof. Specific examples of acrylic acid derivative, methacrylic acid derivatives are methyl acrylate and methacrylate, hydroxyethyl acrylate and methacrylate, ethylene glycol diacrylate and methacrylate, di- or tri- or tetraethylene glycol di-acrylate and methacrylate, glycidyl acrylate and methacrylate, 2,2'-bis(acryloxy and methacryloxyphenyl)propane, 2,2'-bis [4-(3-acryloxy and methacryloxy)-2-hydroxypropoxyphenyl]propane, 1,3-butanediol diacrylate and methacrylate, triacrylic acid and methacrylic acid trimethylolpropane, bisoxyethylenated bisphenol A diacrylate and methacrylate.

Also, if necessary, for adjusting viscosity, curing speed, polymerization shrinkage or the like of monomers or copolymers, oligomers of the compound having the formula (I) or other vinyl monomers may be formulated, and further, inorganic fillers, preferably having particle sizes of 50 μm or less, such as silica, glass beads, aerosil, alumina, silicon nitride, or quartz powder, these inorganic fillers subjected to silane coupling agent, such as γ-methacryloxypropyltrimethoxysilane or vinyltrimethoxysilane, for improving bonding to the resin, or organic composite fillers coated on the filler surface with the above vinyl monomer and other fillers, and curing agents, polymerization inhibitors, colorants, antioxidants, UV-ray absorbers or the like, may be used.

The polymerization and curing of the compound having the formula (I) and a mixture of the compound (I) with another polymerizable monomer copolymerizable therewith, may be carried out by methods such as the chemical polymerization system and photopolymerization system, and in this case, as the curing agent, amines and peroxides may be suitably used for the chemical polymerization, and camphorquinone, benzoin alkyl ether for the photopolymerization.

Although, the amount of the compound having the formula (I) is not particularly limited, when another polymerizable monomer as mentioned above is utilized, it is preferably made 1 to 30% by weight, more preferably 2 to 15% by weight, based on the another polymerizable monomer. If less than 1% by weight, the adhesive effect becomes poor, and the hardness of the cured product may be sometimes lowered if more than 30% by weight is added. The amount of the above another polymerizable monomer formulated should be preferably made 10% to 60% by weight, based on the whole composition, and the amount of the filler formulated should be 40% to 90% by weight, based on the whole composition.

When the dental adhesive composition according to the present invention is used as the adhesive enhancer such as an adhesive liner or bonding agent, preferably the composition is prepared by containing the compound of the formula (I) in 1% to 15% by weight, based on the whole composition, in an organic solvent such as ethanol, ethyl ether, or chloroform, The dental composition can be also prepared by containing the compound of the formula (I) in 1% to 15% by weight, based on the whole composition, in the above another polymerizable monomer or a mixture of the above organic solvent and the above another polymerizable monomer. In these cases, the composition containing the compound having the formula (I) will effect polymerization and curing of the compound having the formula (I) in the presence of a curing agent in the use thereof.

The dental adhesive composition according to the present invention has an excellent adhesiveness to a dental restorative material comprising castable ceramics such as calcium metaphosphate crystallized glass, and further, exhibits a good adhesiveness to teeth and the dental restorative material comprising, for example, an alloy, a porcelain material, a composite resin, and maintains a high adhesiveness even in water and saliva, and therefore, can adhere and firmly and stably fix the dental restorative material to the teeth, whereby the formation of gaps between the teeth and the dental restorative material due to poor adhesion can be prevented and the marginal leakage can be improved to prevent secondary caries.

EXAMPLES

The present invention will now be further illustrated by, but is by no means limited to the following Examples, wherein all parts indicate parts by weight.

EXAMPLE 1

A compound having the above-mentioned formula (I) was dissolved at a concentration of 5% in ethanol a dental adhesive composition (I) was prepared.

Then, each of the enamel surface of bovine teeth embedded in a holder with gypsum, the dental gold-silver-palladium alloy, the nickel-chromium alloy, and a plate with one side of 10 mm and a thickness of 1.5 mm of calcium metaphosphate crystallized glass prepared by casting was finished by a polishing machine to a uniform smooth surface, and these were used as the materials to be adhered. Further, an acrylic resin rod and a stainless steel rod 6 mm in diameter×40 mm in length were finished by a polishing machine to a uniform smooth surface.

Subsequently, the above smooth surface to be attached was treated with 3M phosphoric acid for 30 seconds, washed with water for 30 minutes, and dried by compressed air. The above adhesive composition was applied on the dry teeth surface and, after drying, by using the adhesive (II) with the recipe shown below, the above acrylic resin rod was adhered to a material to be attached, which is the bovine enamel or the calcium metaphosphate crystallized glass, and the above stainless steel rod was also adhered to a material to be attached, which is the gold-silver-palladium alloy or the nickel-chromium alloy. The adhesive strength was measured by a Strograph (manufactured by Toyo Seiki K.K.) (cross head speed=5 mm/min.), for those stored at room temperature and for those stored in artificial saliva at 37° C. for 7 days.

Adhesive (II) recipe:

| Part A | |
|---|---|
| Methyl methacrylate | 2 parts |
| Polymethyl methacrylate | 0.4 parts |
| N,N-dimethyl-p-toluidine | 0.04 parts |
| Part B | |
| Methyl methacrylate | 2 parts |
| Polymethyl methacrylate | 0.4 parts |
| Benzoyl peroxide | 0.04 parts |

Before use, the parts (A) and (B) were mixed at a weight ratio of 1:1.

EXAMPLE 2

Using 5 parts of the compound having the formula (I), 10 parts of methyl methacrylate, 20 parts of diethylene glycol dimethacrylate, 50 parts of bisphenol A-diglycidyl methacrylate, 2 parts of N,N-dimethyl-p-toluidine as the liquid components, these liquid components were mixed with 100 parts of quartz powder with particle sizes of 50μ or less, which had been given a silane coupling treatment, and 1 part of benzoyl peroxide to prepare an adhesive (III). This adhesive was applied on the smooth surfaces of four kinds of materials to be adhered in the same manner as in Example 1, and the adhesive strength of each was measured.

COMPARATIVE EXAMPLES 1-3

Commercially available dental adhesive Chemiace (produced by Sunmedical Co.), Superbond C & B (produced by Sunmedical Co.), and Panavia EX (produced by Kuraray Co.) were applied on the smooth surfaces of four kinds of materials to be adhered in the same manner as in Example 1, and the adhesive strength of each was measured.

The above commercially available dental adhesives have the following compositions.

Chemiace
| | |
|---|---|
| Powder portion: filler | Trimethylolpropane trimethacrylated |
| Liquid portion: | Benzoyl peroxide (i.e., catalyst)<br>Epoxy acrylate resin<br>Methyl methacrylate<br>Diethyl para-toluidine (i.e., catalyst) |
| Adhesive monomer: | 4-META |

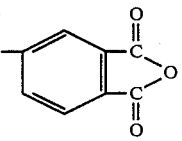

Superbond C & B
| | |
|---|---|
| Powder portion: | Polymethyl methacrylate powder |
| Liquid portion: | Epoxy acrylate resin<br>Methyl methacrylate<br>Tributylborane oxide (i.e., catalyst) |
| Adhesive monomer: | |

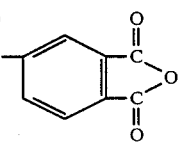

Panavia EX
| | |
|---|---|
| Powder portion: | quartz powder |

| | |
|---|---|
| Liquid portion:<br>Adhesive monomer: | Methyl methacrylate type monomer<br>phenyl P |

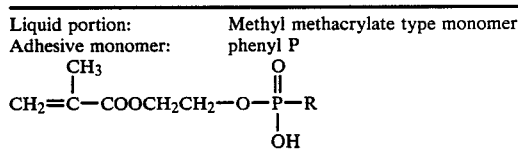

The results of the adhesive measurements as mentioned above are summarized in Table 1.

TABLE 1

Unit: kg/cm²

| | | | Example | | Comparative example | | |
|---|---|---|---|---|---|---|---|
| | | | 1<br>Adhesive (I) +<br>Adhesive (II) | 2<br>Adhesive (III) | 1<br>Chemiace | 2<br>Superbond<br>C & B | 3<br>Panavia<br>EX |
| Material to be attached | Bovine enamel | After 1 day at room temperature | 143 | 138 | 130 | 155 | 145 |
| | | After 7 days in artificial saliva | 100 | 92 | 85 | 121 | 115 |
| | Gold-silver-palladium alloy | After 1 day at room temperature | 198 | 183 | 205 | 220 | 240 |
| | | After 7 days in artificial saliva | 155 | 143 | 185 | 204 | 196 |
| | Nickel-chromium alloy | After 1 day at room temperature | 263 | 250 | 272 | 265 | 300 |
| | | After 7 days in artificial saliva | 190 | 202 | 265 | 232 | 255 |
| | Calcium phosphate crystallized glass | After 1 day at room temperature | 115 | 121 | 75 | 80 | 50 |
| | | After 7 days in artificial saliva | 99 | 102 | 31 | 46 | 6 |

From the results in Table 1, it is clear that the present product has a better adhesiveness to the bovine teeth enamel, the gold-silver-palladium alloy, the nickel-chromium alloy than the adhesive of the prior art, and further, has an excellent adhesiveness to the calcium metaphosphate crystallized glass.

We claim:

1. A dental adhesive composition comprising a compound having the formula (I):

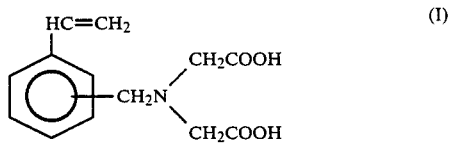

(ii) at least one polymerizable monomer selected from the group consisting of (a) styrene, (b) acrylic acid and derivatives thereof, and (c) methacrylic acid and derivatives thereof and optionally (iii) a solvent.

2. A dental adhesive composition comprising (i) a compound having the formula (I):

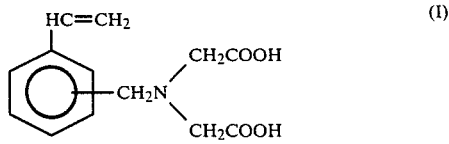

and (ii) a solvent selected from the group consisting essentially of ethanol, ethyl ether and chloroform for the compound having the formula (I).

3. A dental adhesive composition as claimed in claim 2, wherein the concentration of the compound having the formula (I) in the composition is 1% to 15% by weight.

4. A dental adhesive composition as claimed in claim 1, wherein the amount of the compound (i) is 1% to 30% by weight, based on the weight of the polymerizable monomer (ii).

5. A dental adhesive composition as claimed in claim 1, wherein the composition further comprises a solvent selected from the group consisting essentially of ethanol, ethyl ether and chlorofrom for the components (i) and (ii).

6. A dental adhesive composition as claimed in claim 5, wherein the total amount of the components (i) and (ii) in the composition is 10% to 60% by weight.

7. A dental adhesive composition as claimed in claim 4, wherein the amount of the component (i) in the composition is 1% to 15% by weight.

8. A dental adhesive composition as claimed in claim 5, wherein the amount of the component (i) in the composition is 1% to 15% by weight.

9. A dental adhesive composition as claimed in claim 1, wherein the composition further comprises (iii) an inorganic and/or organic filler.

10. A dental adhesive composition as claimed in claim 1, wherein the polymerizable monomer (ii) is a member selected from the group consisting of methyl acrylate and methacrylate, hydroxyethyl acrylate and methacrylate, ethylene glycol diacrylate and methacrylate, di- and tri- and tetraethylene glycol di-acrylate and methacrylate, glycidyl acrylate, and methacrylate, 2,2'-bis(aryloxy and methacryloxyphenyl)propane, 2,2'-bis{4-(3-acryloxy and methacryloxy)-2-hydroxypropoxyphenyl}propane, 1,3-butanediol diacrylate and methacrylate, triacrylic acid and methacrylic acid trimethylolpropane, bisoxyethylenated bisphenol A diacrylate and methacrylate.

11. A dental adhesive composition as claimed in claim 4, wherein the polymerizable monomer (ii) is a member selected from the group consisting of methyl acrylate and methacrylate, hydroxyethyl acrylate and methacrylate, ethylene glycol diacrylate and methacrylate, di- and tri and tetraethylene glycol di-acrylate and methacrylate, glycidyl acrylate and methacrylate, 2,2'-bis(aryloxy and methacryloxyphenyl)propane, 2,2'-bis{4-(3-acryloxy and methacryloxy)-2-hydroxypropoxyphenyl}propane, 1,3-butanediol diacrylate and methacrylate, triacrylic acid and methacrylic acid trimethylolpropane, bisoxyethylenated bisphenol A diacrylate and methacrylate.

12. A dental adhesive composition as claimed in claim 9, wherein the filler (iii) has a particle size of 50 μm or less and is an inorganic filler selected from the group consisting of silica, glass beads, aerosil, alumina, silicon nitride and quartz powder, these inorganic fillers being subjected to a silane coupling agent.

13. A dental adhesive composition as claimed in claim 9, wherein the filler (iii) has a particle size of 50 μm or less and is an inorganic composite filler.

14. A dental adhesive composition as claimed in claim 1, wherein the (N,N-diacrboxymethyl)aminomethyl group in compound (i) is located at the meta- or para-position.

15. A dental adhesive composition as claimed in claim 4, wherein the (N,N-dicarboxymethyl)aminomethyl group in compound (i) is located at the meta- or para-position.

* * * * *